US010729377B2

(12) United States Patent
Wu et al.

(10) Patent No.: US 10,729,377 B2
(45) Date of Patent: Aug. 4, 2020

(54) BASKET-SHAPED CATHETER WITH IMPROVED DISTAL HUB

(71) Applicant: Biosense Webster (Israel) Ltd., Yokneam (IL)

(72) Inventors: Steven Wu, San Jose, CA (US); Sungwoo Min, Fullerton, CA (US); Vishav Aujla, Valencia, CA (US); Neil Merchant, Pasadena, CA (US); Shubhayu Basu, Anaheim, CA (US); Stuart Williams, Ontario, CA (US); Ryan Hoitink, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 293 days.

(21) Appl. No.: 15/956,423

(22) Filed: Apr. 18, 2018

(65) Prior Publication Data

US 2018/0228439 A1     Aug. 16, 2018

Related U.S. Application Data

(62) Division of application No. 15/148,154, filed on May 6, 2016, now Pat. No. 9,974,460.

(51) Int. Cl.
*H05K 3/20* (2006.01)
*A61B 5/00* (2006.01)
(Continued)

(52) U.S. Cl.
CPC .......... *A61B 5/6858* (2013.01); *A61B 5/0422* (2013.01); *A61B 5/6859* (2013.01);
(Continued)

(58) Field of Classification Search
CPC ... A61B 5/6858; A61B 5/6859; A61B 5/0422; A61B 2018/00267; A61B 2562/046;
(Continued)

(56) References Cited

U.S. PATENT DOCUMENTS

| 5,391,199 A | 2/1995 | Ben-Haim |
| 5,397,320 A * | 3/1995 | Essig .................. A61B 17/221 |
| | | 606/110 |

(Continued)

FOREIGN PATENT DOCUMENTS

| EP | 2789366 | 10/2014 |
| WO | 96/05768 | 2/1996 |
| WO | 15/77816 | 6/2015 |

OTHER PUBLICATIONS

European Search Report and Written Opinion for European Application No. 17169779.0, dated Oct. 10, 2017.

(Continued)

*Primary Examiner* — Donghai D Nguyen
(74) *Attorney, Agent, or Firm* — Dergosits & Noah LLP; Todd A. Noah

(57) ABSTRACT

This disclosure is directed to a catheter having a basket-shaped electrode assembly with a high electrode density. The basket-shaped electrode assembly may have a plurality of spines, such as up to twelve, each with a plurality of electrodes, such as up to sixteen. The distal ends of the plurality of spines are joined at a distal hub, all of which are fashioned from a single piece of superelastic material.

20 Claims, 13 Drawing Sheets

(51) Int. Cl.
    *A61B 18/14*       (2006.01)
    *A61B 5/042*       (2006.01)
    *A61B 34/20*       (2016.01)
    *A61B 18/00*       (2006.01)
    *A61M 25/00*       (2006.01)

(52) U.S. Cl.
    CPC ............ *A61B 5/6869* (2013.01); *A61B 18/00* (2013.01); *A61B 18/1492* (2013.01); *A61B 34/20* (2016.02); *A61M 25/0009* (2013.01); *A61B 2018/00267* (2013.01); *A61B 2018/00357* (2013.01); *A61B 2018/00577* (2013.01); *A61B 2018/00839* (2013.01); *A61B 2034/2051* (2016.02); *A61B 2562/0209* (2013.01); *A61B 2562/046* (2013.01); *A61B 2562/187* (2013.01); *A61B 2562/222* (2013.01); *Y10T 29/49222* (2015.01)

(58) Field of Classification Search
    CPC ... A61B 2562/187; A61B 2018/00285; A61M 25/0009; Y10T 29/49124; Y10T 29/49128; Y10T 29/49208; Y10T 29/49222
    USPC .................................. 29/829, 831, 876, 884
    See application file for complete search history.

(56) References Cited

U.S. PATENT DOCUMENTS

| | | |
|---|---|---|
| 5,772,590 A | 6/1998 | Webster, Jr. |
| 6,064,905 A | 5/2000 | Webster et al. |
| 6,216,044 B1 * | 4/2001 | Kordis ................. A61B 5/0422 607/122 |
| 6,239,724 B1 | 5/2001 | Doron et al. |
| 6,332,089 B1 | 12/2001 | Acker et al. |
| 6,484,118 B1 | 11/2002 | Govari |
| 6,500,182 B2 * | 12/2002 | Foster ................. A61B 17/221 606/127 |
| 6,618,612 B1 | 9/2003 | Acker et al. |
| 6,690,963 B2 | 2/2004 | Ben-Haim et al. |
| 6,748,225 B1 | 6/2004 | Kepler |
| 6,973,340 B2 | 12/2005 | Fuimaono et al. |
| 8,825,130 B2 | 9/2014 | Just et al. |
| 9,408,663 B2 | 8/2016 | Hall et al. |
| 2001/0029371 A1 | 10/2001 | Kordis |
| 2002/0065455 A1 | 5/2002 | Ben-Haim et al. |
| 2003/0120150 A1 | 6/2003 | Govari |
| 2004/0068178 A1 | 4/2004 | Govari |
| 2013/0172715 A1 | 7/2013 | Dale et al. |
| 2014/0305699 A1 | 10/2014 | Govari |
| 2014/0309512 A1 | 10/2014 | Govari et al. |
| 2015/0223757 A1 | 8/2015 | Werneth et al. |
| 2015/0342532 A1 | 12/2015 | Basu et al. |

OTHER PUBLICATIONS

U.S. Appl. No. 13/860,921, filed Apr. 11, 2013, entitled High Density Electrode Structure.
U.S. Appl. No. 14/063,477, filed Oct. 25, 2013, entitled Connection of Electrodes to Wires Coiled on a Core.
Office Action for U.S. Appl. No. 15/148,154, dated Sep. 12, 2017.
Office Action for U.S. Appl. No. 15/148,154, dated Jun. 6, 2017.
Office Action for U.S. Appl. No. 15/148,154, dated Feb. 28, 2017.

* cited by examiner

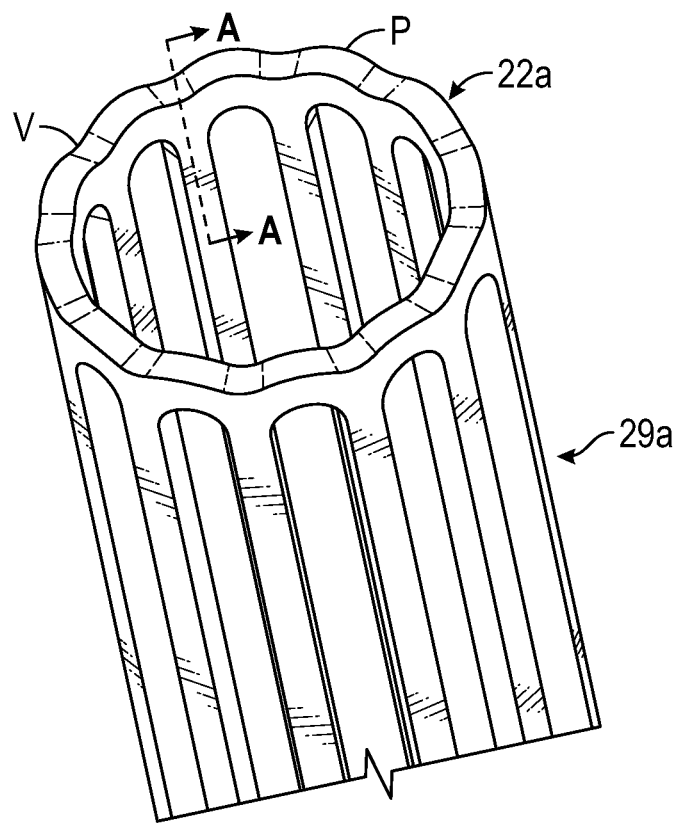
FIG. 8A
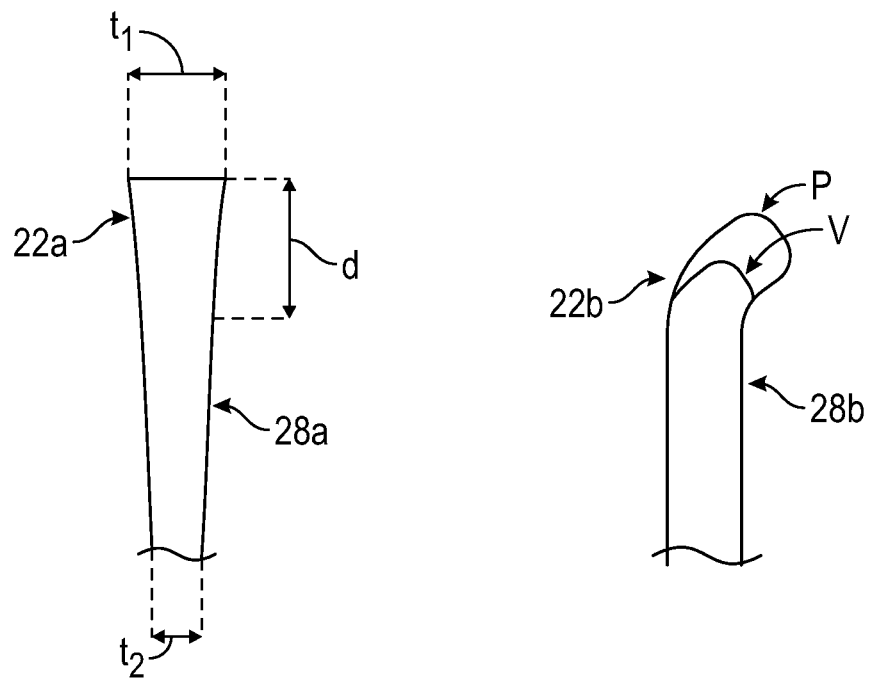
FIG. 8B  FIG. 8C

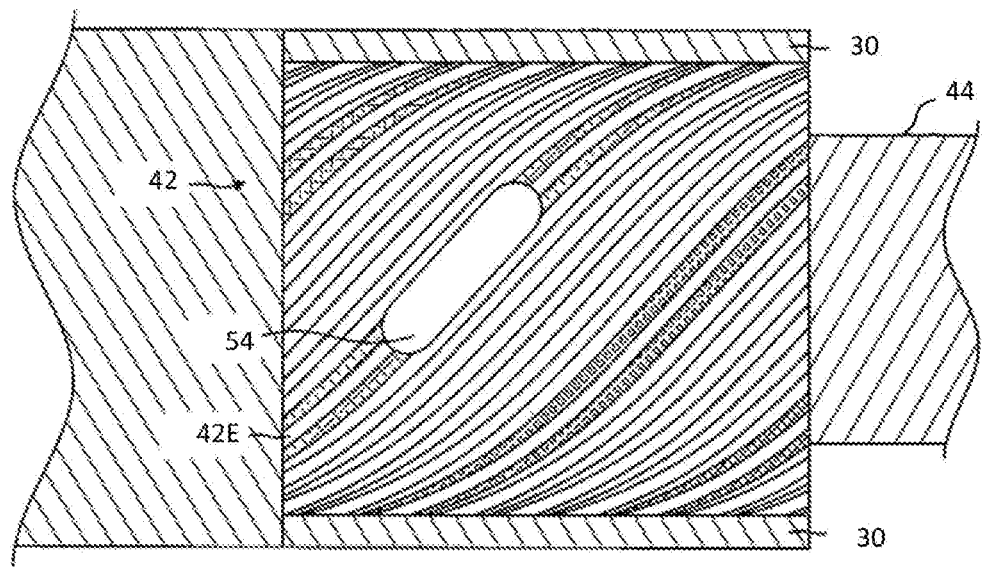
FIG. 16A
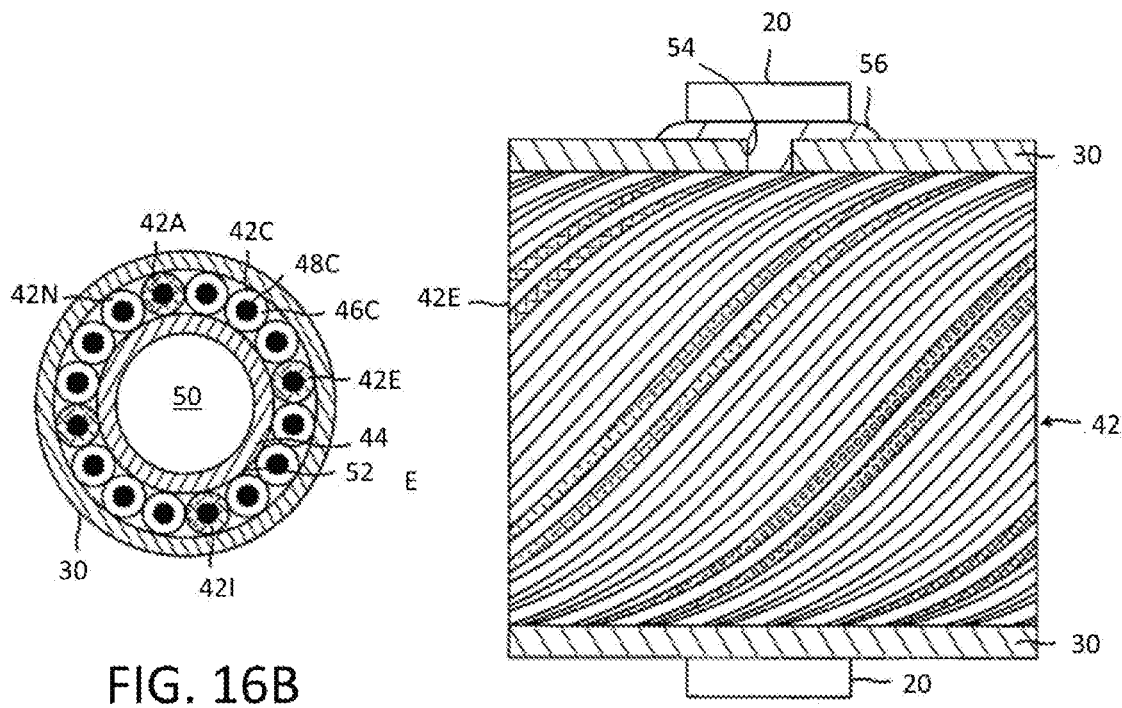
FIG. 16B
FIG. 16C

BASKET-SHAPED CATHETER WITH IMPROVED DISTAL HUB

CLAIM OF PRIORITY AND RELATED APPLICATION DATA

This application is a divisional of U.S. application Ser. No. 15/148,154 filed on May 6, 2016, which is incorporated herein by reference in its entirety and for all purposes.

FIELD OF THE PRESENT DISCLOSURE

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748, 255 and 6,973,340, the entire disclosures of each of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body.

It is desirable that a basket assembly be capable of detecting in as few beats as possible, including a single beat, as much of the electrical function of the region in which the electrode assembly is deployed, such as the left or right atrium as possible. By implementing a greater number of electrodes in the electrode assembly, correspondingly greater and more complete coverage of the region may be obtained. Further, the increased number of electrodes may reduce or eliminate the need to reposition the electrode assembly to access all of the desired area in the region. Often, increasing the number of electrodes corresponds with an increase in the number of spines or other structures that support the electrodes. These spines are joined at a distal end by a central hub. As the device is deployed, a number of the distal electrodes may be put in a position that they are not in contact with the tissue.

Additionally, the increase in the number of spines generally relates to an increase in the length and diameter of an elongated distal hub that is used to connect the spines. Devices that have a larger distal hub may be harder to deliver and deploy within a patient and may increase the risk of trauma to the tissue. Another problem with prior art distal hubs is that the movement from a delivery state to a deployed state causes stress in the structure as it transitions. This stress may cause undesirable damage to the device. As such, there is a need for a basket-shaped electrode assembly having an increased electrode density while maintaining a sufficiently minimized distal hub diameter and length that will improve the deployment and electrode contact within a chamber of a patient's heart and decrease the stress to the material as the device transitions to the deployed configuration. The techniques of this disclosure satisfy this and other needs as described in the following materials.

SUMMARY

The present disclosure is directed to a catheter including an elongated catheter body extending along a longitudinal axis, the elongated catheter body having a proximal end and a distal end, a flexible wire assembly positioned at the distal end of the elongated catheter body formed from a single piece of shape memory material, the flexible wire assembly having a plurality of flexible wires, each flexible wire having a proximal end and a distal end and a distal hub, the distal hub extending from the distal ends of at least a portion of the plurality of flexible wires and a plurality of spines formed from the plurality of flexible wires. The catheter further includes a plurality of electrodes and cabling attached to each spine, the plurality of electrodes and cabling having a corresponding plurality of wires coiled on a core and covered by a sheath such that each electrode is attached through the sheath to one of the plurality of wires, such that the catheter has one operational state wherein the spines bow radially outwardly and another operational state wherein the spines are arranged generally along a longitudinal axis of the catheter body.

In one aspect, the distal hub further includes at least one stress-relieving edge.

In one aspect, at least a portion of the shape memory material of the stress-relieving edge comprises a first thickness at a distal end and tapering to a second thickness at the distal end of the flexible wire.

In one aspect, the stress-relieving edge further includes a radius of curvature, the radius of curvature directed toward an inner diameter of the distal hub.

In one aspect, the plurality of flexible wires further includes a bridge portion, the bridge portion connecting the distal end of the flexible wires to the distal hub.

In one aspect, the distal ends of two adjacent flexible wires form a bridge portion, the bridge portion connecting the flexible wires to the distal hub. The bridge portion may have a linear or sinusoid shape.

In one aspect, the distal hub is a waveform, the wave form further includes a plurality of U-shaped indentations or sinusoidal shaped indentations, wherein each indentation is placed between adjacent flexible wires. The indentations define a gap, the gap having a first distance when in the delivery configuration and a second distance when in the deployed configuration.

In one aspect, the distal hub is a continuous ribbon shaped waveform, the wave form includes a plurality of distal indentations, where each distal indentation is placed between adjacent flexible wires and extends distally from the distal ends of the flexible wires. The ribbon shaped distal hub has a plurality of distal indentations that are distally oriented and a plurality of proximal indentations that are proximally oriented, wherein the distal indentations and proximal indentations alternate and are evenly spaced around a circumference of the distal hub.

In one aspect, the distal hub has a first stress relieving edge and a second stress relieving edge, the first stress relieving edge has a waveform shape on a distal end of the distal hub, and the second stress relieving edge has an arched shape on a proximal edge of the distal hub, the distal hub further includes at least two distal projections, wherein the distal projections are evenly distributed around a circumference of the distal hub.

In one aspect, a catheter is made by the steps of forming an elongate catheter body, forming a flexible wire assembly from a single piece of shape memory material, the flexible wire assembly having a plurality of flexible wires joined at a distal hub and forming a stress-relieving edge onto a distal end of the distal hub at a location opposite of the plurality of flexible wires. The catheter is further made by heating the flexible wire assembly to heat set a basket-shaped arrangement, connecting a plurality of electrodes and cabling to each of the plurality of flexible wires to form a basket-shaped electrode assembly and connecting the basket shaped electrode assembly to a distal end of the elongate catheter body.

In one aspect, the single piece of shape memory material is a nitinol alloy tube.

In one aspect, the stress relieving edge may be a bridge portion connecting the flexible wires to the distal hub, or a continuous waveform, the continuous waveform having a plurality of indentations or may include a plurality of distal projections.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which:

FIG. 8a is a schematic view of a distal end of a flexible wire assembly in a delivery configuration, according to one embodiment.

FIGS. 8b and 8c are cross sections of the distal hub of the flexible wire assembly of FIG. 8a, according to one embodiment.

FIG. 16A is a top view of a cabling of a spine of a basket-shaped electrode assembly with part(s) broken away, according to one embodiment.

FIG. 16B is an end cross-sectional view of the cabling of FIG. 16A.

FIG. 16C is a side view of the cabling of FIG. 16A, with part(s) broken away.

DETAILED DESCRIPTION

Figure 1:
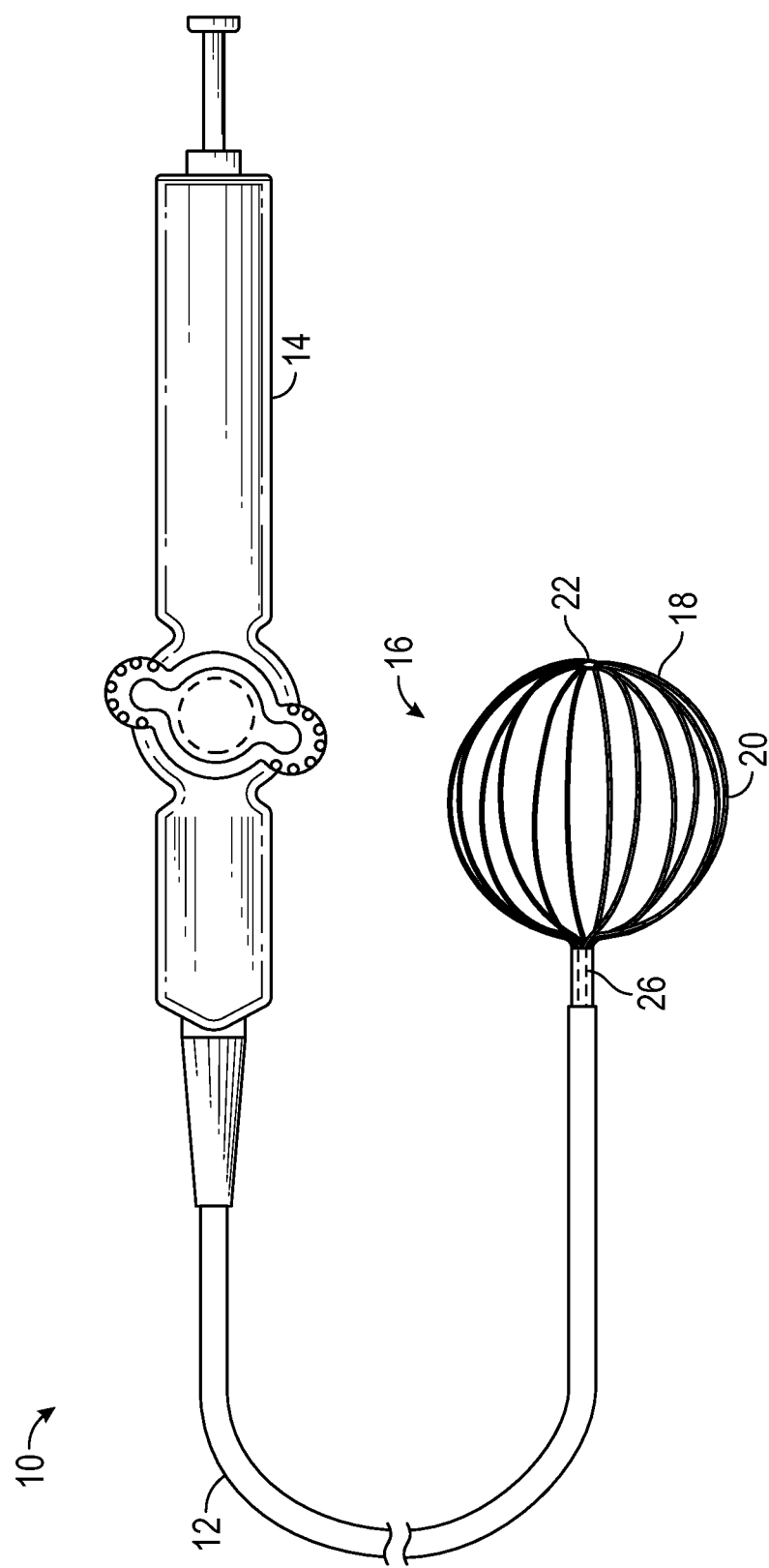
FIG. 1 is a top plan view of a catheter of the present invention, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a", "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts.

Such electrical activity is random from beat to beat. To analyze or 'map' this type of electrical activity, it is desirable to obtain the 'picture' as quickly as possible, such as within one heartbeat. In other words, all the points of the map or picture may be obtained simultaneously within one-tenth of a second. According to the techniques of this disclosure, a basket-shaped electrode assembly having a high electrode density with improved electrode-to-tissue contact may be used to accurately map this electrical activity.

As shown in FIG. 1, the catheter 10 comprises an elongated catheter body 12 having proximal and distal ends and a control handle 14 at the proximal end of the catheter body, with a basket-shaped electrode assembly 16 having a plurality of spines 18, each carrying multiple electrodes 20, mounted at the distal end of the catheter body 12. The catheter body 12 comprises an elongated tubular construction having a single, axial or central lumen 26, but can optionally have multiple lumens if desired. To enable accurate mapping of electrical signals, for example to detect most or substantially all of the electrical function of the right or left atrium in as little as a single heartbeat, it may be desirable to provide an array of electrodes with a relatively high density. As such, the number of spines 18 employed may be six, eight, ten, twelve or any other suitable number. The distal ends of spines 18 are joined together at a distal hub 22. Distal hub 22 is a generally circular and flat structure to allow for more of the electrodes 20 to contact the tissue to be mapped. Spines 18 may be evenly or unevenly distributed radially about distal hub 22. Further, each spine 18 may include multiple electrodes 20, such as at least eight and up to approximately 16 electrodes per spine. Similarly, the electrodes may be evenly distributed along the spine or may be skewed proximally, centrally or distally to facilitate analysis of the measured electrical signals.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner The outer diameter of the catheter body 12 is not critical, but generally should be as small as possible and may be no more than about 10 french depending on the desired application. In one aspect, the overall diameter of the catheter body 12 may relate to the number of electrodes 20 implemented by basket-shaped electrode assembly 16 in order to accommodate the associated electrical leads. For example, a twelve-spine design with each spine carrying sixteen electrodes for a total of 192 electrodes, a ten-spine design with each spine carrying sixteen electrodes for a total of 160 electrodes and an eight-spine design with each spine carrying sixteen electrodes for a total of 128 electrodes may utilize up to a 10.0 french catheter body. Likewise the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

Figure 2:
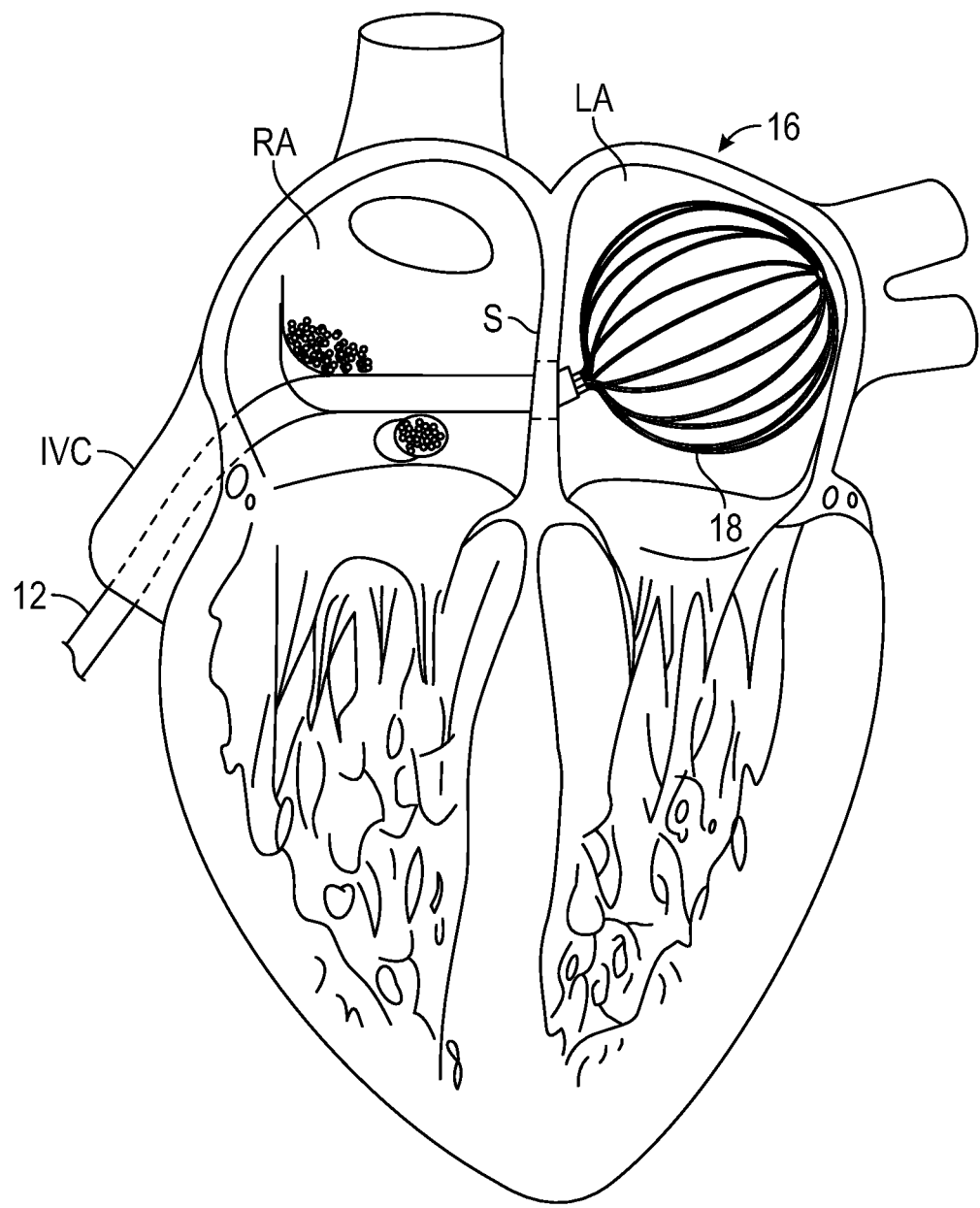
FIG. 2 is a schematic view of the basket-shaped electrode assembly of FIG. 1 deployed in the left atrium.

Spines 18 include a shape memory material, as described below, that facilitates assuming an expanded arrangement. As shown in FIG. 2, when the basket-shaped electrode assembly 16 assumes the expanded configuration, spines 18 bow outwards into contact or closer proximity with the walls of the chamber in which it has been deployed, such as the left atrium.

In one aspect, an electrophysiologist may introduce a guiding sheath, guidewire and dilator into the patient, as is generally known in the art. As an example, a suitable guiding sheath for use in connection with the inventive catheter is a 10 french DiRex™ Guiding Sheath (commercially available from BARD, Murray Hill, N.J.). The guidewire is inserted, the dilator is removed, and the catheter is introduced through the guiding sheath whereby the guidewire lumen 26 permits the catheter to pass over the guidewire. In one exemplary procedure as depicted in FIG. 2, the catheter is first introduced to the right atrium (RA) via the inferior vena cava (IVC), where it passes through the septum (S) in order to reach the left atrium (LA).

As will be appreciated, the guiding sheath covers the spines 18 of the basket-shaped electrode assembly 16 in a collapsed position so that the entire catheter can be passed through the patient's vasculature to the desired location. Once the distal end of the catheter reaches the desired location, e.g., the left atrium, the guiding sheath is withdrawn to expose the basket-shaped electrode assembly 16. Upon withdrawal of the guiding sheath, the shape memory material of the basket-shaped electrode assembly radially expands the device within the chamber. With the basket-shaped electrode assembly 16 radially expanded, the ring electrodes 20 contact atrial tissue. As recognized by one skilled in the art, the basket-shaped electrode assembly 16 may be fully or partially expanded, straight or deflected, in a variety of configurations depending on the configuration of the region of the heart being mapped.

When the basket-shaped electrode assembly 16 is expanded, the electrophysiologist may map local activation time and/or ablate using electrodes 20, which can guide the electrophysiologist in diagnosing and providing therapy to the patient. The catheter may include one or more reference ring electrodes mounted on the catheter body and/or one or more reference electrodes may be placed outside the body of the patient. By using the catheter with the multiple electrodes on the basket-shaped electrode assembly, the electrophysiologist can obtain a true anatomy of a cavernous region of the heart, including an atrium, allowing a more rapid mapping of the region.

As used herein, the term "basket-shaped" in describing the electrode assembly 16 is not limited to the depicted configuration, but can include other designs, such as spherical or egg-shaped designs, that include a plurality of expandable arms or spines connected, directly or indirectly, at their proximal and distal ends. In one aspect, different sized basket-shaped electrode assemblies may be employed depending on the patient's anatomy to provide a close fit to the area of the patient being investigated, such as the right or left atria.

Figure 3:
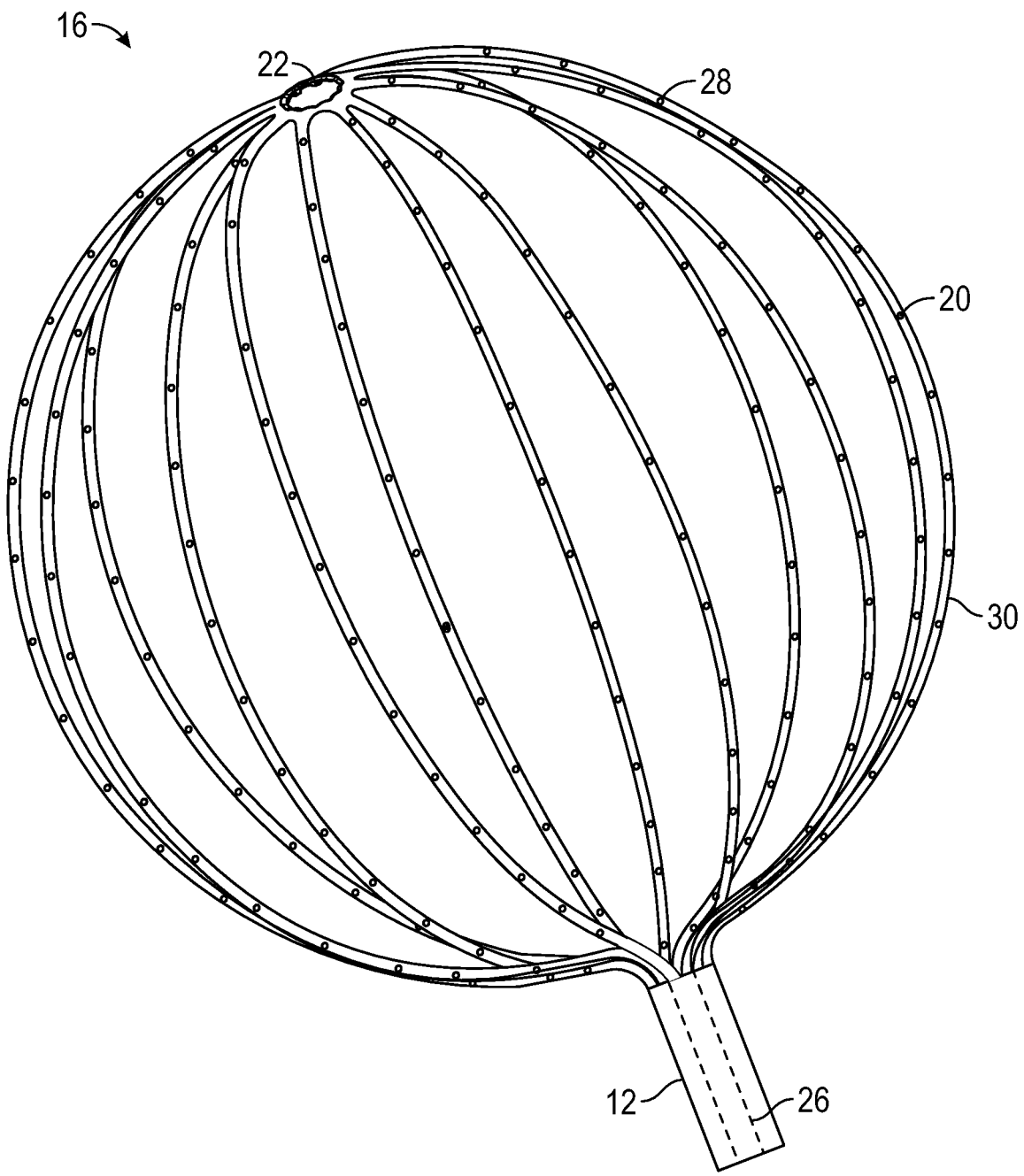
FIG. 3 is a schematic view of a basket-shaped electrode assembly, according to one embodiment.

A detailed view of one embodiment of the basket-shaped electrode assembly 16 is shown in FIG. 3, featuring a total of twelve spines 18, each carrying sixteen electrodes 20. As noted above, in other embodiments, different numbers of spines 18 and/or electrodes 20 may be employed, each of which may be evenly or unevenly distributed as desired. The distal ends of the spines 18 are joined at distal hub 22. Correspondingly, the proximal ends of the spines 18 may be secured to the distal end of the catheter body 12. Lumen 26 may be used as a guidewire lumen. In some embodiments, lumen 26 may also be used to supply a suitable irrigation fluid, such as heparinized saline, to the basket-shaped electrode assembly 16. A fitting (not shown) in the control handle 14 may be provided to conduct irrigation fluid from a suitable source or pump into the lumen 26.

Each spine 18 may comprise a flexible wire 28 with a non-conductive covering 30 on which one or more of the ring electrodes 20 are mounted. In an embodiment, the flexible wires 28 may be formed from a shape memory material to facilitate the transition between expanded and collapsed arrangements and the non-conductive coverings 30 may each comprise a biocompatible plastic tubing, such as polyurethane or polyimide tubing. A plurality of flexible wires 28 may be joined to form a flexible wire assembly 29.

Figure 4:
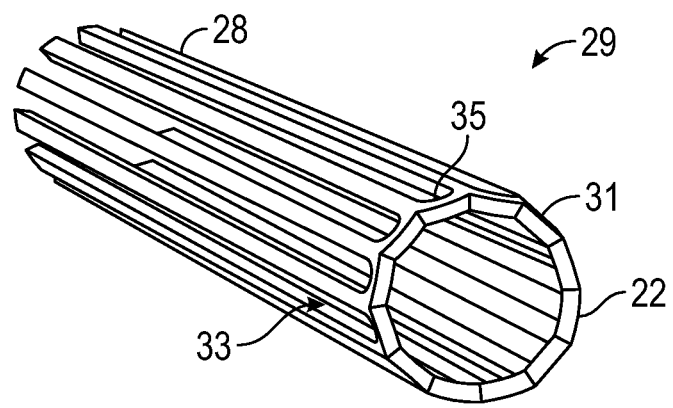
FIG. 4 is a schematic view of a flexible wire assembly of the basket-shaped electrode assembly of FIG. 3.
Figure 5:
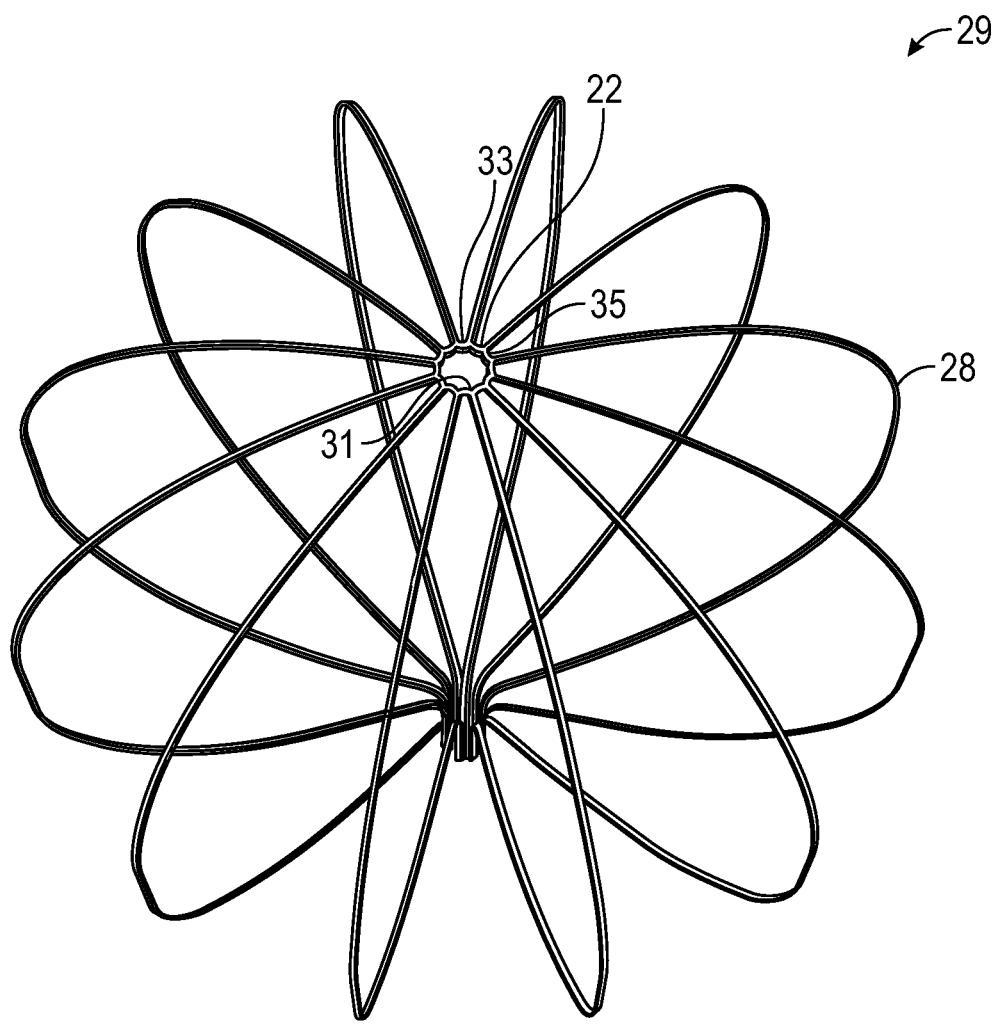
FIG. 5 is a schematic view of an expanded flexible wire assembly of the basket-shaped electrode assembly, according to one embodiment.

FIGS. 4 and 5 illustrate one embodiment of a flexible wire assembly 29. Flexible wire assembly 29 comprises a plurality of flexible wires 28. The distal ends of each flexible wire 28 are joined at distal hub 22. In one embodiment, flexible wire assembly 29 is composed of Nitinol, a nickel-titanium alloy. As illustrated in FIG. 4, in one embodiment, flexible wire assembly 29 is formed from a single cylindrical tube of nitinol. In this embodiment, the nitinol tube has an outer diameter of 2.59 mm (0.102 inch) and an inner diameter of 2.18 mm (0.086 inch). In one example, the outer diameter is no greater than 10 french. Additionally, in an embodiment, the nitinol tube has a length between 1 mm (0.039 inch) and 20 mm (0.79 inch) that is sufficient to form the spines. One of ordinary skill in the art will appreciate that the length of the spines may vary and will correspond to the size of the chamber into which the device is deployed.

As mentioned above, the flexible wire assembly 29 is formed from a single tube. In one embodiment the nitinol tube is cut using standard cutting techniques such as laser cutting or etching. In another embodiment, an appropriate drill may be used to trace a pattern into a nitinol tube and then a laser may be used to complete the pattern in the nitinol tube. Other known methods of forming the nitinol tube into the flexible wire assembly 29 may be used. Using an appropriate laser, the flexible wires 28 and distal hub 22 are cut from the tube as a single unit. The individual flexible wires 28 are cut into the tube leaving material that will form the distal hub 22. In one embodiment, the height of the distal hub 22 is the same dimension as the thickness of the nitinol tube from which the assembly is cut. In this embodiment, the height of the distal hub 22 is reduced as compared to the prior art. During use, this reduction in height translates to a distal hub having a reduced dimension when in the deployed configuration. The reduced dimension of the distal hub 22 may allow more of the electrodes in close proximity to the distal hub 22 to come in contact with the chamber, making the mapping of the chamber faster and more accurate.

The process of forming the tube into the flexible wire assembly 29 also includes forming at least one stress-relieving edge 31 on hub 22. The stress-relieving edge 31 is a shaped edge to facilitate movement of the basket-shaped electrode assembly 16 from a delivery arrangement to a deployed arrangement. As illustrated in FIGS. 4 and 5, the stress relieving edge 31 comprises a scalloped shaped edge on the distal end of the flexible wire assembly 29. The formation of this edge reduces the amount of material of the distal hub. This reduction of material allows for the spines to expand into the basket-shape with a lesser amount of stress on the distal hub 22. It will be appreciated that as the flexible wires 28 expand into the basket-shape, the shaped edge 31 of the distal end of the distal hub moves, or rotates, inwardly to become an inner diameter of the deployed distal hub 22. In so doing, the deployed inner diameter of the distal hub 22 reduces in size as the basket-shaped device is formed. Thus, the removal of this material in forming the distal hub 22 will reduce the stress and strain on the hub as it is moved from the delivery arrangement to the deployed arrangement. In an additional step in forming the distal hub 22, any sharp edges on the scalloped edge may be smoothed in order to prevent tissue damage during use. Other geometries for this stress-relieving edge are discussed in more detail below in relation to FIG. 8a to FIG. 15 and may include, for example, a wave form edge, a tabbed edge, or a truncated pyramid edge.

FIGS. 4 and 5 further illustrate that a proximal portion 33 of the distal hub 22 may include a second stress relieving edge 35. In one embodiment, as electrode assembly 16 moves from a delivery configuration (FIG. 4) to a deployed configuration (FIG. 5) the proximal portion 33 of distal hub 22 becomes the outer diameter of the deployed distal hub. To further reduce the stress from the movement of the device during deployment, additional material from the proximal edge of the distal hub may be removed. As an example, the space between spines may have a semicircular or arch shape, as shown in FIG. 5. So, as the inner diameter of the distal hub decreases during expansion of the flexible wires 28, the outer diameter of the proximal portion 33 of the hub increases. Removal of the outer diameter material between the flexible wires 28 will further reduce the stress during this process. In another embodiment, the distal hub 22 of the flexible wire assembly 29 may be annealed to increase flexibility. The increase in flexibility may further reduce the stress on the distal hub as it transitions into the deployed configuration.

The geometry of the flexible wire assembly 29 also reduces the stress caused by the manufacturing process. Heat treatment of the flexible wire assembly 29, once the device is formed into the basket-shape, creates a heat-treatment stress. This stress is reduced due to the geometry of the distal hub 22. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape",(e.g. the basket-shape), that is dependent on its temperature phases. The austenite phase is nitinol's stronger, higher-temperature phase, with a simple cubic crystalline structure. Superelastic behavior occurs in this phase (over a 50°-60° C. temperature spread). FIG. 5 illustrates the flexible wire assembly 29 in the "memorized shape" or basket-shape. During manufacture, the nitinol tube (FIG. 4) is heated and formed into the basket-shape. This shape is then heat set, as is known in the art. Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, the basket-shaped electrode assembly 16 may have a three dimensional shape that can be easily collapsed to be fed into a guiding sheath and then readily returned to its expanded shape memory configuration upon delivery to the desired region of the patient upon removal of the guiding sheath.

FIGS. 4 and 5 illustrate a device cut from a single nitinol tube. In other embodiments, the flexible wire assembly 29 is manufactured from a sheet of nitinol material, shaped and heat set into the desired "memorized" shape.

Figure 6:
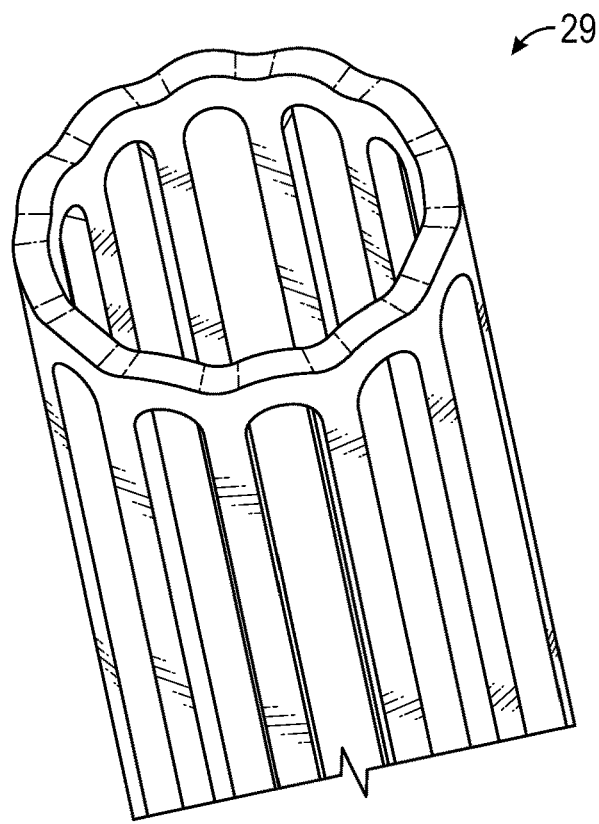
FIG. 6 is a schematic view of a distal end of a flexible wire assembly in a delivery configuration, according to one embodiment.
Figure 7:
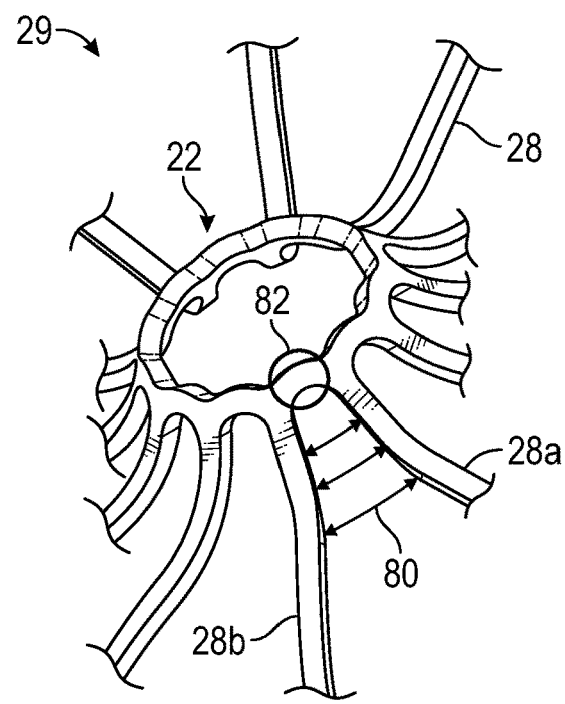
FIG. 7 is a schematic view of a distal end of a flexible wire assembly in a deployed configuration, according to one embodiment.

Referring now to FIGS. 6 and 7, FIG. 6 illustrates a distal portion of a flexible wire assembly 29 in an unexpanded relaxed state. In this state, there is no stress or strain on the device since it is still in a natural tube shape. FIG. 7 illustrates the same distal portion of the flexible wire assembly 29 in an expanded shape. As the flexible wires 28 move outwardly, as indicated by arrows 80, stress is concentrated at the distal hub 22. In an example, as flexible wires 28a and 28b expand, the stress is concentrated at a peak, indicated by circle 82, as the peak is forced into a smaller space. In this example, for each pair of adjacent flexible wires, the stress is concentrated at the peak where the flexible wires join the distal hub. The concentrated stress in the distal hub may be reduced by the various distal hub designs described below and illustrated in FIGS. 8a to 15.

FIG. 8a illustrates another embodiment of a flexible wire assembly 29a in an unexpanded state. In one embodiment to reduce the stress on distal hub 22a, the distal hub may include areas of increased thickness to increase the rigidity of the distal hub. FIG. 8b illustrates a cross-section of a flexible wire 28a and a portion of distal hub 22a taken along line A-A of FIG. 8a. In this embodiment, the portion of distal hub 22a that extends above flexible wire 22a has an increased thickness (t1) as compared to the thickness of the flexible wire (t2). In this embodiment, the thickness (t1) of the distal hub 22a tapers proximally along distance (d) from the distal edge of distal hub 22a toward the distal end of flexible wire 28a. This increase in thickness may be included in the entire distal hub 22a or just a portion of distal hub 22a. For example, the increased thickness (t1) may be limited to the areas of the distal hub between adjacent flexible wires, the peaks (indicated by "P"), or it may be limited to the areas of the distal hub extending from the flexible wire, the valley (indicated by "V"). FIG. 8c illustrates another embodiment of distal hub 22b having an increased thickness as well as being slightly curved inward. In other embodiments, the distal hub may only include an inward curve without the added thickness. In these embodiments, the inward curving distal hub forms a radius of curvature that may further reduce the dimensions of the deployed distal hub as well as reduce any trauma to the tissue the device may come into contact.

FIG. 9 to FIG. 15 each illustrate various geometries of the distal hub that may also reduce the stress on the distal hub as it moves from the delivery configuration to the deployed configuration. In each of these embodiments, the distal hub 22 and/or the flexible wires 28 are configured to reduce the stress that is transferred from the flexible wires 28 to the distal hub 22 when the flexible wires are expanded.

Figure 9:
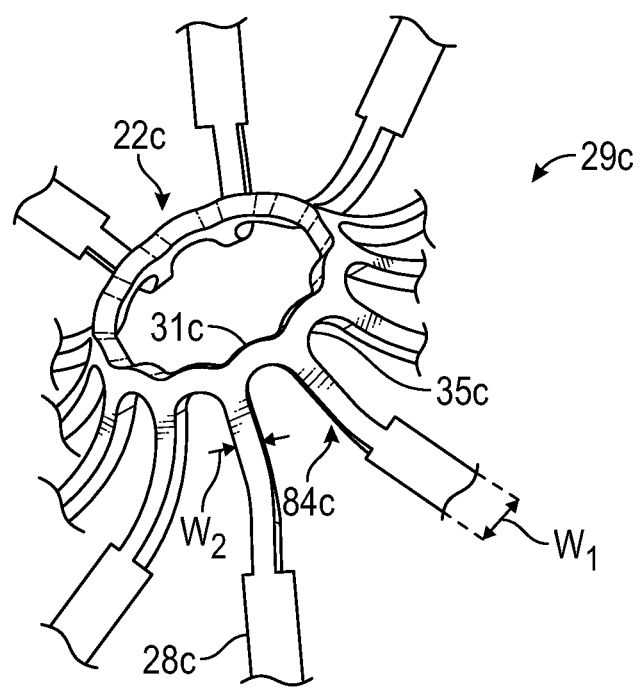
FIG. 9 is a schematic view of a portion of a distal end of a flexible wire assembly in a deployed configuration, according to one embodiment.

FIG. 9 illustrates another embodiment of flexible wire assembly 29c having a distal hub 22c with a reduced stress configuration. In this embodiment, distal hub 22c includes a first stress-relieving edge 31c having a waveform or scalloped shape, as described above. Additionally, distal hub 22c also includes a second stress-relieving edge 35c. In this embodiment, the second stress relieving edge includes reconfigured flexible wire junctions with the distal hub 22c. Flexible wire assembly 29c comprises a plurality of flexible wires 28c, each having a main body portion including a first width (w1) and a bridge portion (bridge) 84c having a decreased width (w2) where the flexible wire 28c joins the distal hub 22c. In this embodiment, mechanical stress on the distal hub 22c is decreased due to the reduction of width of the flexible wires to w2 where they join the distal hub. It was found that the reduction of stress on the hub improves the overall robustness of the flexible wire assembly.

Figure 10:
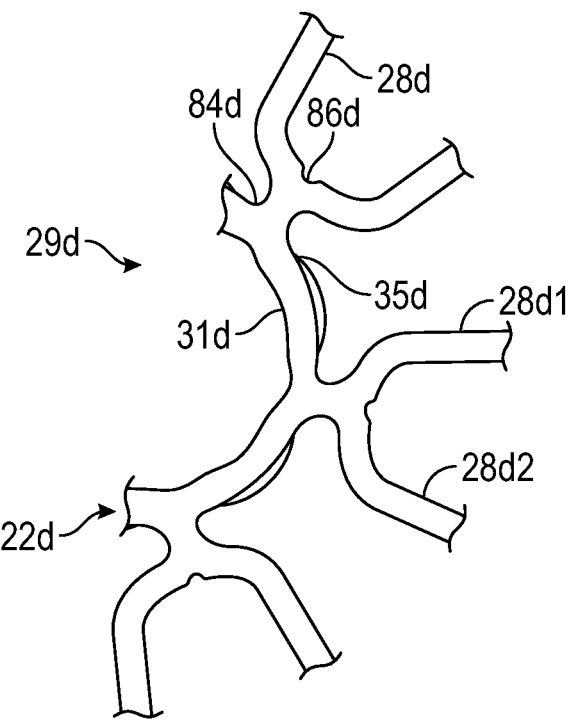
FIG. 10 is a schematic view of a portion of a distal end of a flexible wire assembly in a deployed configuration, according to one embodiment.

FIG. 10 illustrates another embodiment of a flexible wire assembly 29d having a distal hub 22d with a reduced stress configuration. In this embodiment, distal hub 22d includes a first stress-relieving edge 31d having a waveform or scalloped shape, as described above. Distal hub 22d further includes another configuration of a second stress-relieving edge 35d. In this embodiment, the second stress relieving edge includes reconfigured flexible wire junctions with the distal hub 22d. In this embodiment, each pair of flexible wires, e.g. flexible wires 28d1 and 28d2, joins the distal hub 22d via a bridge 84d. In this embodiment, the nitinol tube is cut in such a way as to reduce the number of flexible wires 28d that join the distal hub 22d. For example, in a flexible wire assembly having twelve flexible wires, six bridges are formed to connect these wires to the distal hub 22d. By reducing the overall number of connections to the distal hub, there is a reduction of mechanical stress on the distal hub. Additionally, in this embodiment, the second stress relieving edge may include a scalloped or waveform pattern, as described above, for additional reduction in stress load. To further reduce the stress on the distal hub 22d, the flexible wires 28d may include an indentation 86d. This indentation 86d is located at the junction where each pair of wires joins together. This indentation 86d is formed from removing material from between the flexible wires, which allows the wires to expand more freely when moving from a delivery configuration to a deployed configuration. The reduction of stress at this point of the flexible wire assembly 28d further reduces the stress on the distal hub 22d.

Figure 11:
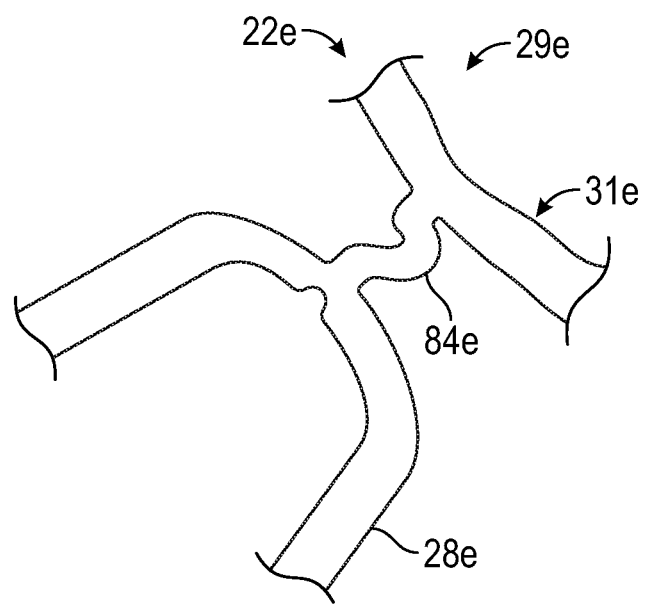
FIG. 11 is a schematic view of a portion of a distal end of a flexible wire assembly in a deployed configuration, according to one embodiment.

FIG. 11 illustrates another embodiment of a flexible wire assembly 29e having a distal hub 22e with a reduced stress configuration. In this embodiment, the bridge 84e joining the distal hub 22e with a pair of flexible wires 28e comprises a sinusoid shape as compared to the linear shape of bridge 84d of FIG. 10. In all other aspects, this embodiment is the same as that described above for FIG. 10.

Figure 12A:
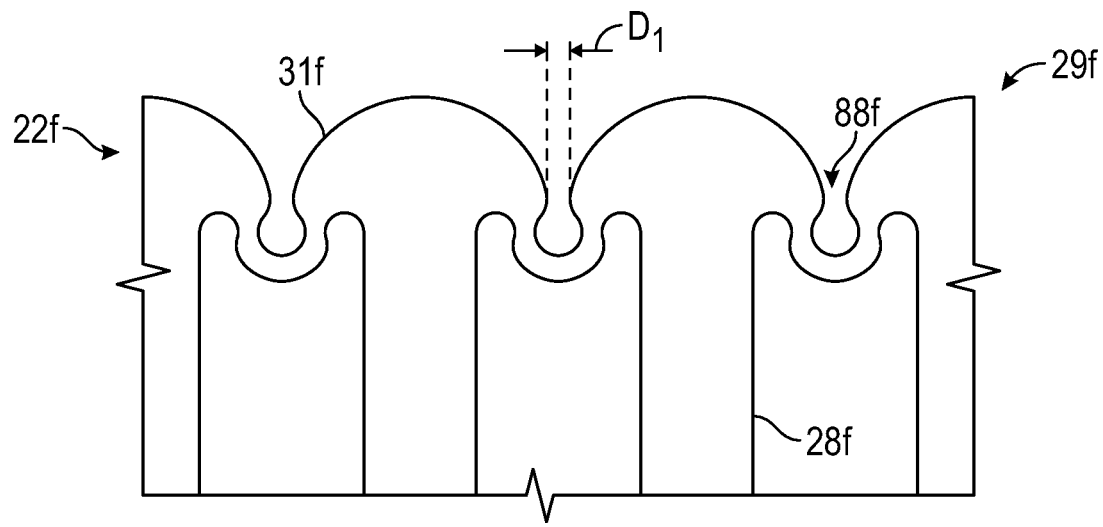
FIGS. 12a and 12b are schematic views of a portion of a distal end of a flexible wire assembly in a delivery configuration and deployed configuration, respectively, according to one embodiment.
Figure 12B:
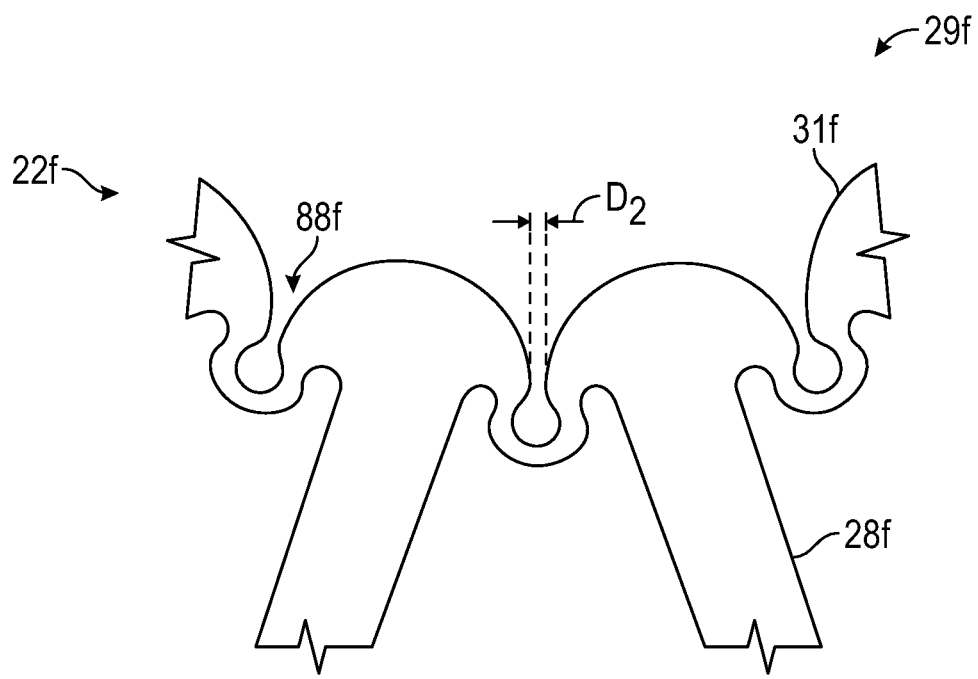
Figure 13A:
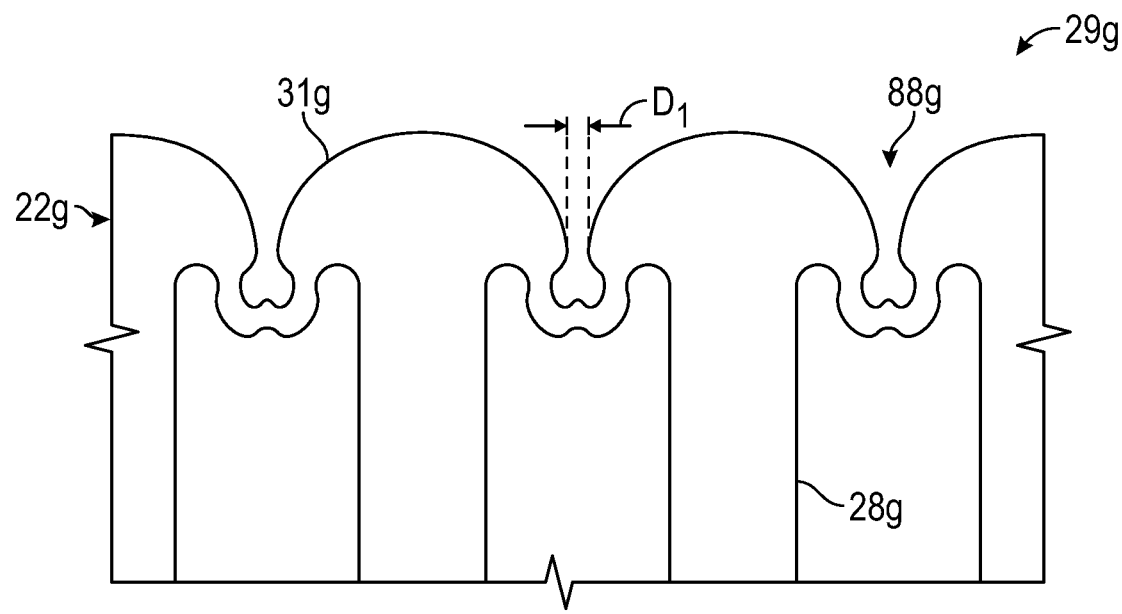
FIGS. 13a and 13b are schematic views of a portion of a distal end of a flexible wire assembly in a delivery configuration and deployed configuration, respectively, according to one embodiment.
Figure 13B:
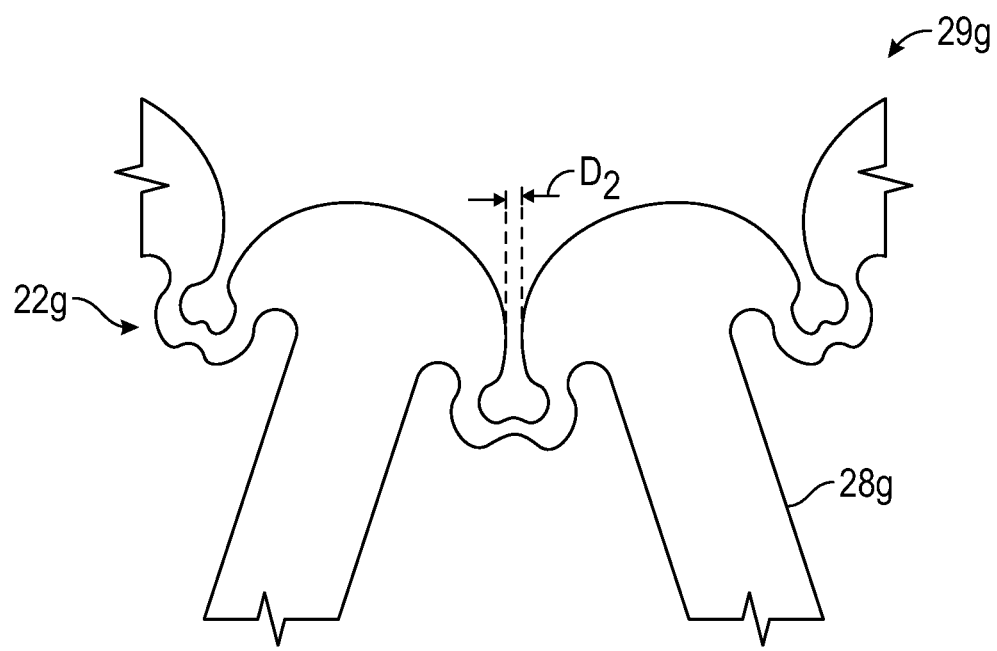

FIGS. 12a and 12b illustrate another embodiment of flexible wire assembly 29f having a distal hub 22f with a reduced stress configuration. In this embodiment, distal hub 22f includes a first stress-relieving edge 31f having a waveform or scalloped shape. FIG. 12a illustrates flexible wire assembly 29f in a delivery configuration and FIG. 12b illustrates flexible wire assembly 29f in a deployed configuration. As shown in FIG. 12a, distal hub 22f is configured to include a waveform edge having "U"-shaped indentations 88f located between each pair of adjacent flexible wires 28f. U-shaped indentation 88f has a gap having a first distance D1 in a delivery configuration and a second distance D2 in a deployed configuration. In this embodiment, as the flexible wires 28f are expanded during deployment, the gap of the U-shaped indentation reduces from D1 to D2. It is this change in formation of the U-shaped indentation that absorbs the stress caused by the expansion of the flexible wire assembly. FIGS. 13a and 13b illustrate another embodiment of flexible wire assembly 29g having a distal hub 22g with a reduced stress configuration similar to that of FIGS. 12a and 12b. However, in this embodiment, the indentation 88g is more of a sinusoidal configuration. In all other aspects, the flexible wire assembly 29g is similar as that described above for FIGS. 12a and 12b.

Figure 14:
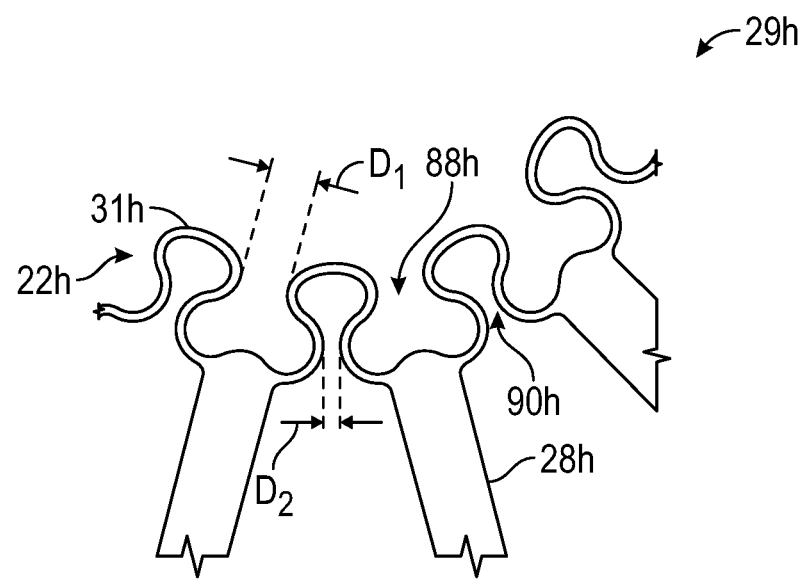
FIG. 14 is a schematic view of a portion of a distal end of a flexible wire assembly in a deployed configuration, according to one embodiment.

FIG. 14 illustrates another embodiment of flexible wire assembly 29h having a distal hub 22h with a reduced stress configuration. In this embodiment, distal hub 22h includes a first stress-relieving edge 31h having a continuous ribbon-like waveform shape. In this embodiment, the waveform extends distally from the distal ends of the flexible wires 28h. The ribbon shaped distal hub 22h form a plurality of distal indentations 88h that alternate with a plurality of proximal indentations 90h. Distal indentations 88h have a gap distance D1 that reduces in dimension as the flexible wire assembly is deployed. Proximal indentations 90h have a gap distance D2 that increases in dimension as the flexible wire assembly is deployed. In this embodiment, the ribbon shaped distal hub 22h absorbs the stress when the flexible wire assembly transitions from a delivery configuration to a deployed configuration.

Figure 15:
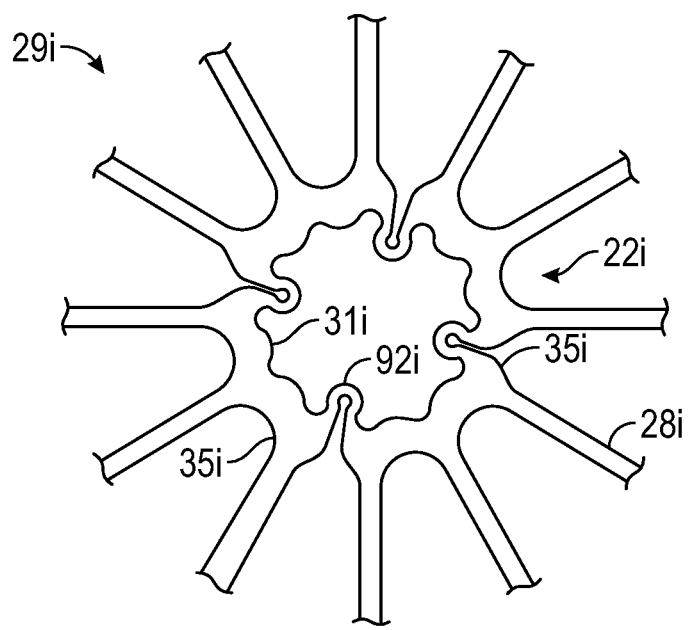
FIG. 15 is a schematic view of a portion of a distal end of a flexible wire assembly in a deployed configuration, according to one embodiment.

FIG. 15 illustrates another embodiment of a flexible wire assembly 29i having a distal hub 22i with a reduced stress configuration. In this embodiment, distal hub 22i includes a first stress-relieving edge 31i having a generally waveform or scalloped shape and a second stress-relieving edge 35i having an arch-shaped configuration, as described above. In addition, the distal hub 22h further includes a plurality of distal projections 92i. The number of distal projections may vary. FIG. 15 illustrates four distal projections, but there may be as few as two and as many as eight. In this embodiment, the distal projections 92i are evenly distributed around the circumference of distal hub 22i. In a delivery configuration, these distal projections 92i extend distally from the distal end of the flexible wire assembly.

In the deployed state, these distal projections rotate inwardly as the distal hub rotates inwardly, as described above. In the embodiment illustrated in FIG. 15, there are shown four distal projections 92i, one for each group of three flexible wires 28i. One with ordinary skill in the art will recognize that the number and position may vary depending on the application and the total number of flexible wires.

One of ordinary skill in the art will appreciate that elements of each of the embodiments described above for FIGS. 3 to 15 may be combined with other elements from other embodiments and these combinations are within the scope of the invention. For example, the stress relieving edge 31d of the distal hub 22d illustrated in FIG. 10 may further include the inward curve of 22b to further reduce the distal hub profile in the deployed configuration. The following discussion of FIGS. 16 to 17 also applies to each of the above described embodiments.

In a further aspect, each spine 18 may include cabling 40 with built-in or embedded lead wires 42 for the electrodes 20 carried by the spine as shown in FIGS. 16A-C. The cabling has a core 44, and a plurality of generally similar wires 42 each covered by an insulating layer 46 that enables each wire to be formed and to function as a conductor 48. The core 44 provides a lumen 50 in which can pass other components such as a support structure in the form of flexible wire 28 and/or additional lead wire(s), cables, tubing or other components.

In the following description, generally similar components associated with cabling 40 are referred to generically by their identifying component numeral, and are differentiated from each other, as necessary, by appending a letter A, B, . . . to the numeral. Thus, wire 42C is formed as conductor 48C covered by insulating layer 46C. While embodiments of the cabling may be implemented with substantially any plurality of wires 42 in the cabling, for clarity and simplicity in the following description cabling 40 is assumed to comprise N wires 42A, 42B, 42C, . . . 42N, where N equals at least the number of ring electrodes on each respective spine 18 of the basket-shaped electrode assembly 16. For purposes of illustration, insulating layers 46 of wires 42 have been drawn as having approximately the same dimensions as conductors 48. In practice, the insulating layer is typically approximately one-tenth the diameter of the wire.

The wires 42 are formed over an internal core 44, which is typically shaped as a cylindrical tube. The core material is typically selected to be a thermoplastic elastomer such as a polyether block amide or PEBAX®. Wires 42 are formed on an outer surface 52 of the core 44 by coiling the wires around the tube. In coiling wires 42 on the surface 52, the wires are arranged so that they contact each other in a "close-packed" configuration. Thus, in the case that core 44 is cylindrical; each wire 42 on the outer surface is in the form of a helical coil, configured in a multi-start thread configuration. For example, in the case of the N wires 42 assumed herein, wires 42 are arranged in an N-start thread configuration around core 44.

In contrast to a braid, all helical coils of wires 42 herein have the same handedness (direction of coiling). Moreover, wires in braids surrounding a cylinder are interleaved, so are not in the form of helices. Because of the non-helical nature of the wires in braids, even braid wires with the same handedness do not have a threaded form, let alone a multi-start thread configuration. Furthermore, because of the lack of interleaving in arrangements of wires in embodiments of the cabling, the overall diameter of the cabling produced is less than that of cabling using a braid, and the reduced diameter is particularly beneficial when the cabling is used for a catheter.

Once wires 42 have been formed in the multi-start thread configuration described above, the wires are covered with a protective sheath, such as in the form of the non-conductive covering 30 described above. The protective sheath material is typically selected to be a thermoplastic elastomer such as for example, 55D PEBAX without additives so that it is transparent. In that regard, the insulating layer 46 of at least one of wires 42 may be colored differently from the colors of the remaining wires as an aid in identifying and distinguishing the different wires.

The process of coiling wires 42 around the core 44, and then covering the wires by the non-conductive covering 30 essentially embeds the wires within a wall of cabling 40, the wall comprising the core and the sheath. Embedding the wires within a wall means that the wires are not subject to mechanical damage when the cabling is used to form a catheter. Mechanical damage is prevalent for small wires, such as 48AWG wires, if the wires are left loose during assembly of a catheter.

In use as a catheter, an approximately cylindrical volume or lumen 50 enclosed by the core 44, that is afforded by embedding smaller wires (such as the 48 AWG wires) in the wall, allows at least a portion of the lumen 50 to be used for other components. It is understood that the plurality of wires 42 shown in the drawings is representative only and that a suitable cabling provides at least a plurality of wires equal to or greater than the plurality of ring electrodes mounted on each cabling or spine of the assembly. Cabling suitable for use with the present invention is described in U.S. application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the entire disclosures of which have been incorporated above. Each cabling 40 (with embedded lead wires 42) may extend to the control handle 14 for suitable electrical connection of wires 42, thereby allowing signals measured by electrodes 20 to be detected.

As noted, each spine 18 and cabling 40 pair carries a plurality of ring electrodes 20, which may be configured as monopolar or bipolar, as known in the art. Cabling 40 is schematically shown by a top view in FIG. 16A and by a side view in FIG. 16C, in which portions of non-conductive covering 30 have been cut away to expose wires 42 of the cabling 40, as well as to illustrate the attachment of a ring electrode 20 to the cabling 40. FIG. 16A illustrates cabling 40 prior to attachment of electrode 20, while FIG. 16C illustrates the cabling after the ring electrode has been attached. The ring electrodes 20 may have suitable dimensions to allow them to be slid over sheath 54.

The attachment point for each electrode 20 may be positioned over one or more of the wires 42, such as wire 42E in the illustrated example. A section of non-conductive covering 30 above the wire 42E and a corresponding section of insulating layer 46E are removed to provide a passage 54 to conductor 48E. In a disclosed embodiment, conductive cement 56 may be fed into the passage, ring electrode 20 may then be slid into contact with the cement, and finally the electrode may be crimped in place. Alternatively, the ring electrode 20 may be attached to a specific wire 42 by pulling the wire through non-conductive covering 30, and resistance welding or soldering the ring electrode to the wire.

In another embodiment, basket-shaped electrode assembly may include an expander. The expander (not shown) may comprise a wire or hypotube formed from a suitable shape memory material, such as a nickel titanium alloy. As will be appreciated, different relative amounts of movement of the expander 22 along the longitudinal axis may affect the degree of bowing, such as to enable the spines 18 to exert greater pressure on the atrial tissue for better contact between the tissue and the electrodes on the spines. Thus, a user can change the shape of the electrode assembly by adjusting the longitudinal extension or withdrawal of the expander.

Figure 17:
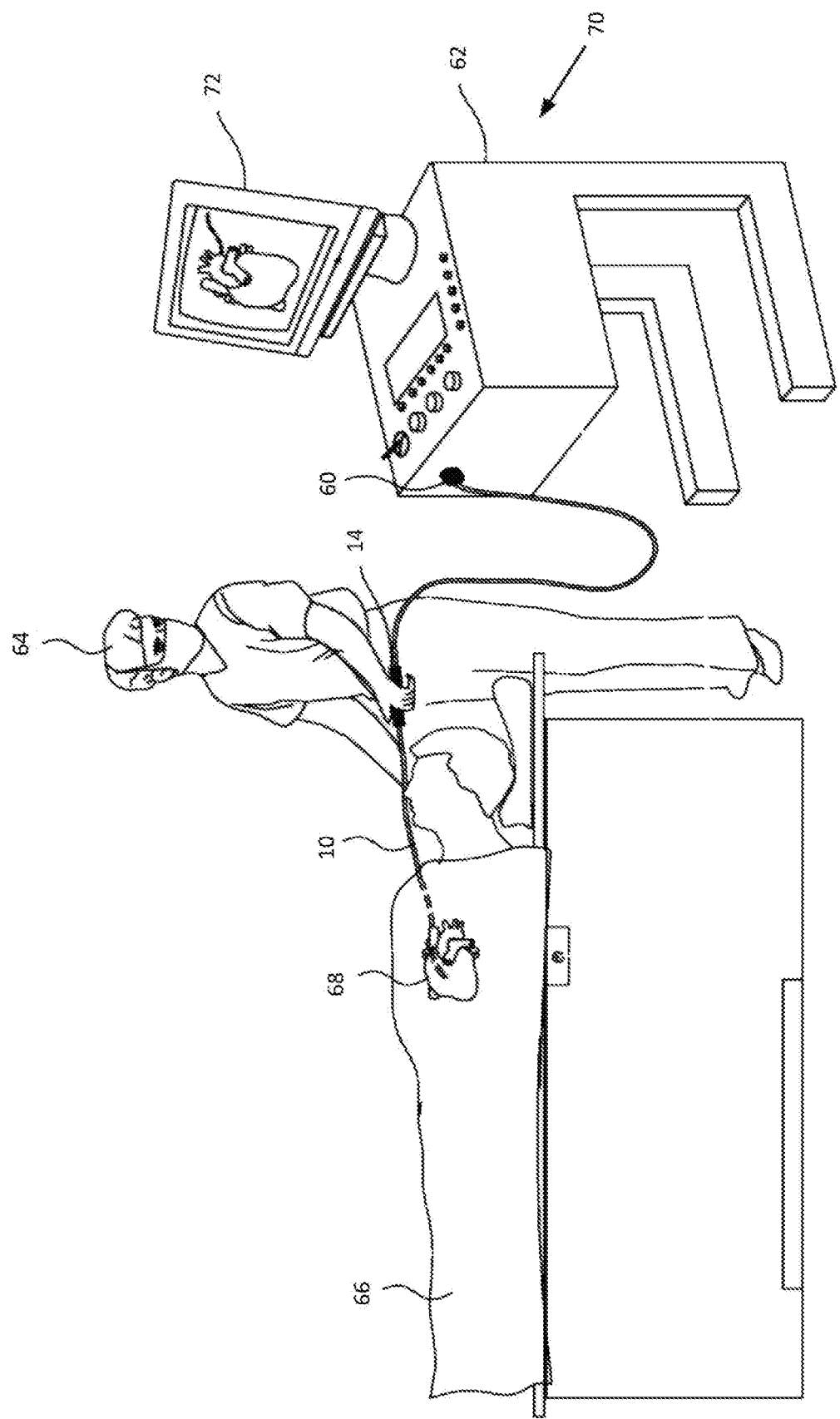
FIG. 17 is a schematic illustration of an invasive medical procedure using a basket-shaped electrode assembly, according to one embodiment.

To help illustrate use of the basket-shaped electrode assembly 16, FIG. 17 is a schematic depiction of an invasive medical procedure, according to an embodiment of the present invention. Catheter 10, with the basket-shaped electrode assembly 16 (not shown in this view) at the distal end may have a connector 60 at the proximal end for coupling the wires 42 from their respective electrodes 20 (neither shown in this view) to a console 62 for recording and analyzing the signals they detect. An electrophysiologist 64 may insert the catheter 10 into a patient 66 in order to acquire electropotential signals from the heart 68 of the patient. The professional uses the control handle 14 attached to the catheter in order to perform the insertion. Console 62 may include a processing unit 70 which analyzes the received signals, and which may present results of the analysis on a display 72 attached to the console. The results are typically in the form of a map, numerical displays, and/or graphs derived from the signals. With the inventive catheter, the map from the basket-shaped electrode assembly 16 is improved due to the reduction in the distal hub 22 dimensions, allowing more of the electrodes to contact the chamber.

In a further aspect, the processing unit 70 may also receive signals from one or more location sensors 74 provided near a distal end of the catheter 10 adjacent the basket-shaped electrode assembly 16 as schematically indicated in FIG. 1. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 70 to determine the position, (e.g., the location and orientation) of the distal end of catheter 10 within the heart cavity. The electrophysiologist may then view the position of the basket-shaped electrode assembly 16 on an image the patient's heart on the display 72. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally of the basket-shaped electrode assembly 16. The coordinates of the distal sensor relative to the proximal sensor may be determined and, with other known information pertaining to the curvature of the spines 18 of the basket-shaped electrode assembly 16, used to find the positions of each of the electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for forming a catheter comprising:
    forming an elongate catheter body;
    forming a flexible wire assembly from a single piece of shape memory material, the flexible wire assembly having a plurality of flexible wires joined at a distal hub;
    forming a stress-relieving edge onto a distal end of the distal hub at a location opposite of the plurality of flexible wires;
    heating the flexible wire assembly to heat set a basket-shaped arrangement;
    connecting a plurality of electrodes and cabling to each of the plurality of flexible wires to form a basket-shaped electrode assembly; and
    connecting the basket shaped electrode assembly to a distal end of the elongate catheter body.

2. The method of claim 1, wherein the single piece of shape memory material comprises a nitinol alloy tube.

3. The method of claim 1, wherein the stress relieving edge comprises a bridge portion connecting the flexible wires to the distal hub.

4. The method of claim 3, wherein the bridge portion comprises a sinusoid shape.

5. The method of claim 3, wherein the bridge portion comprises a linear shape.

6. The method of claim 1, wherein the stress relieving edge comprises a continuous waveform, the continuous waveform having a plurality of indentations.

7. The method of claim 1, wherein the distal hub comprises a waveform, the wave form further comprising a plurality of U-shaped indentations, wherein each U-shaped indentation is placed between adjacent flexible wires.

8. The method of claim 7, wherein the U-shaped indentations define a gap, the gap having a first distance when in a delivery configuration and a second distance when in a deployed configuration.

9. The method of claim 1, wherein the distal hub comprises a waveform, the wave form further comprising a plurality of sinusoidal-shaped indentations, wherein each sinusoidal-shaped indentation is placed between adjacent flexible wires.

10. The method of claim 9, wherein the sinusoidal-shaped indentations define a gap, the gap having a first distance when in the delivery configuration and a second distance when in the deployed configuration.

11. The method of claim 1, wherein the distal hub comprises a continuous ribbon shaped waveform, the wave form further comprising a plurality of distal indentations, wherein each distal indentation is placed between adjacent flexible wires and extends distally from the distal ends of the flexible wires.

12. The method of claim 11, wherein the distal hub has a plurality of distal indentations that are distally oriented and a plurality of proximal indentations that are proximally oriented, wherein the distal indentations and proximal indentations alternate and are evenly spaced around a circumference of the distal hub.

13. The method of claim 1, wherein the distal hub has a first stress relieving edge and a second stress relieving edge, wherein the first stress relieving edge has a waveform shape on a distal end of the distal hub, and the second stress relieving edge has an arched shape on a proximal edge of the distal hub, the distal hub further comprising at least two distal projections, wherein the distal projections are evenly distributed around a circumference of the distal hub.

14. The method of claim 1, wherein the stress-relieving edge comprises a plurality of distal projections.

15. The method of claim 1, wherein the stress-relieving edge further includes a radius of curvature, the radius of curvature directed toward an inner diameter of the distal hub.

16. A method for forming a catheter comprising:
    forming an elongate catheter body, the elongated catheter body having a proximal end and a distal end;
    forming a flexible wire assembly positioned at the distal end of the elongated catheter body from a single piece of shape memory material, the flexible wire assembly having a plurality of flexible wires, each flexible wire having a proximal end and a distal end, the flexible wire assembly further having a distal hub extending from the distal ends of at least a portion of the plurality of flexible wires, the distal hub configured to be generally parallel to the longitudinal axis of the elongated catheter body when the catheter is in a first operational state and generally perpendicular to the longitudinal axis of the elongated catheter body when the catheter is in a second operational state;
    forming a stress-relieving edge onto a distal end of the distal hub at a location opposite of the plurality of flexible wires;
    heating the flexible wire assembly to heat set a basket-shaped arrangement;
    connecting a plurality of electrodes and cabling to each of the plurality of flexible wires to form a basket-shaped electrode assembly; and
    connecting the basket shaped electrode assembly to a distal end of the elongate catheter body.

17. The catheter of claim 16, wherein the single piece of shape memory material comprises a nitinol alloy tube.

18. The catheter of claim 16, wherein the stress relieving edge comprises a bridge portion connecting the flexible wires to the distal hub.

19. The catheter of claim 16, wherein the stress relieving edge comprises a continuous waveform, the continuous waveform having a plurality of indentations.

20. The catheter of claim 16, wherein the stress-relieving edge comprises a plurality of distal projections.

\* \* \* \* \*